United States Patent [19]

Voss et al.

[11] Patent Number: 5,066,640
[45] Date of Patent: Nov. 19, 1991

[54] PHENYLETHL O-METHYLCINNAMATE, A PROCESS FOR PREPARATION AND A FRAGRANCE COMPOSITION CONTAINING SAME

[75] Inventors: Erdmuthe Voss; Werner Moschinsky; Doris Hofmann-Moritz, all of Munich, Fed. Rep. of Germany

[73] Assignee: Consortium fur elektrochemische Industrie GmbH, Munich, Fed. Rep. of Germany

[21] Appl. No.: 350,577

[22] Filed: May 11, 1989

[30] Foreign Application Priority Data

May 13, 1988 [DE] Fed. Rep. of Germany ....... 3816452

[51] Int. Cl.$^5$ ................................................. A61K 7/46
[52] U.S. Cl. ........................................ 512/21; 560/104
[58] Field of Search ........................... 560/104; 512/21

[56] References Cited

U.S. PATENT DOCUMENTS

| 2,246,974 | 6/1941 | Coleman et al. | 560/104 |
| 3,074,891 | 1/1963 | Kulka | 560/104 |
| 4,263,359 | 5/1981 | Anderson et al. | 560/104 |
| 4,587,260 | 5/1986 | Smerbeck et al. | 560/104 |

OTHER PUBLICATIONS

Bohlmann et al., Chem. Abst., vol. 87, #35864h (1977).
Ninomiya et al., Chem. Abst., vol. 92, #31935n (1980).
Furia et al., "Fenaroli's Handbook of Flavor Ingredients", 2nd Edtn., vol. 2, p. 463 (1975).

Primary Examiner—James H. Reamer
Attorney, Agent, or Firm—Collard, Roe & Galgano

[57] ABSTRACT

The invention relates to phenylethyl o-methylcinnamate and a process for its preparation. Phenylethyl o-methylcinnamate is prepared by, first, alkylating ethyl acetoacetate with o-methylbenzyl chloride in the presence of a phase transfer catalyst to yield 2-(o-methylbenzyl)-acetoacetate. Thereafter the 2-(o-methylbenzyl)-acetoacetate yielded in the alkylating step is halogenated to yield ethyl 2-halo-2-(o-methylbenzyl)-acetoacetate. This is followed by degarding the ethyl 2-halo-2-(o-methylbenzyl)-acetoacetate acid. Finally the o-methylcinnamic acid obtained in the degarding step is esterified with 2-phenylethanol into phenylethyl o-methylcinnamate. A fragrance composition utilizing phenylethyl o-methylcinnamate is also disclosed.

3 Claims, No Drawings

PHENYLETHL O-METHYLCINNAMATE, A PROCESS FOR PREPARATION AND A FRAGRANCE COMPOSITION CONTAINING SAME

The present invention relates to phenylethyl o-methylcinnamate (systematic name: 2-phenylethyl 3-(2-methylphenyl)-2-propenoate), a process for its preparation and a fragrance composition containing the same.

Like cinnamaldehydes or cinnamyl alcohols, cinnamates are widely used in perfumery, as well as in the aroma and flavor industry. They are used for formulating, imitating or fixing floral perfume compositions, as, for example, in the composition of lily-of-the-valley, rose, lilac, gardenia or hyacinth fragrances (cf. S. Arctander, *Perfume and Flavor Chemicals*, Montclair, N.J. (USA), 1969).

In the imitation of natural fragrance carriers, it is of course the declared aim of the perfumer to imitate these so that the result is as deceptively similar as possible to the natural example. This object is made more difficult if the corresponding essential oils cannot be obtained without decomposition or are very expensive, and in this case synthetic substitutes, substitutes which are identical to natural ones or even those which are not identical to natural ones therefore represent a useful tool for the perfumer. Moreover, unimagined effects can be achieved with such substitutes, even in compositions not otherwise found in nature, i.e., fantasy compositions.

It is, therefore, an object of the present invention to provide a compound that may be used in a fragrance composition, which may be produced inexpensively and efficiently and which is capable of increasing the heavy floral accents in floral and fantasy perfume compositions.

The foregoing and related objects are achieved by a perfume fragrance which includes the compound phenylethyl o-methylcinnamate. It has been found, surprisingly, that the introduction of an o-methyl substituent at the phenyl group of the acid component of phenylethyl cinnamate gives a fragrance material which, in contrast to the conventional cinnamates, is capable of substantially increasing the heavy floral accents in floral and fantasy perfume compositions and of reinforcing the natural floral fragrance with exalting full-bodied fragrance.

In a process for the preparation of phenylethyl o-methylcinnamate, ethyl acetoacetate is alkylated with o-methylbenzyl chloride using a phase transfer catalyst.

Other preferred embodiments of this process are the halogenation of the resulting ethyl 2-(o-methylbenzyl)-acetoacetate, reaction of the resulting ethyl 2-halo-2-(o-methylbenzyl)-acetoacetate with bases and esterification of the resulting o-methylcinnamic acid with 2-phenylethanol.

The process described starts from the base chemicals ethyl acetoacetate and o-methylbenzyl chloride, which are available industrially on a large scale. The other reactants are also commercially available products.

The alkylation of ethyl acetoacetate with o-methylbenzyl chloride using a phase transfer catalyst can be carried out both with quaternary ammonium salts, such as, for example, tetrabutylammonium bromide, and with crown ethers, such as, for example, 18-crown-6. The bases used may be both alkali metal hydroxides, preferably sodium hydroxide and alkali metal carbonates, preferably potassium carbonate. The reaction is carried out at elevated temperature, preferably at 70° to 90° C.

Halogenation of the resulting ethyl 2-(o-methylbenzyl)-acetoacetate is preferably carried out using the elemental halogens or other halogenating agents, in particular sulfuryl chloride. The preferred temperature range for this reaction is between 25° and 60° C., most preferably 40° to 55° C.

The degradation of the ethyl 2-halo-2-(o-methylbenzyl)-acetoacetate to o-methylcinnamic acid preferably takes place under the action of bases, such as potassium hydroxide or sodium hydroxide. The acid thus obtained is preferably converted into the phenylethyl ester by azeotropic esterification.

Phenylethyl o-methylcinnamate is used as a fragrance material. The compound according to the invention is distinguished by a powerful, floral, warm, heavy fragrance resembling acacia, narcissus or tuberose.

If, instead of conventional cinnamates, such as, for example, phenylethyl cinnamate, linalyl cinnamate, etc., 10% of the compound according to the invention is added to linear floral compositions-such as, lilac and gardenia-the natural full-bodied fragrance of the floral initial odor, middle odor and in particular the after odor of the compositions is substantially enriched and reinforced. The intensity and warmth of the floral compositions are increased. By adding the compound according to the invention, the floral accents are reinforced with a natural, exalting body. The fragrance intensity, the excellent adhesion and the brilliant fixing capacity distinguish the compound according to the invention from other cinnamates.

The present invention will now be described in greater detail by way of the following examples. It should, of course, be understood that the following examples are intended as being merely illustrative of the present invention and are not intended as a means for defining the scope thereof.

EXAMPLE 1

Ethyl 2-(o-methylbenzyl)-acetoacetate 344 g (2.45 moles) of o-methylbenzyl chloride and 3.5 moles of 25% strength aqueous NaOH solution were added dropwise to a refluxed, thoroughly stirred solution of 455 g (3.5 moles) of ethyl acetoacetate, 35 g (0.11 moles) of tetrabutylammonium bromide and 1.2 liters of toluene in the course of 2 hours, simultaneously from two dropping funnels. Thereafter, stirring was continued for a further 2 hours with refluxing. After the reaction solution had cooled, water was added, the phases were separated and the organic phase was washed once with water, once with dilute phosphoric acid and again with water and was then stirred with solid sodium bicarbonate. The mixture was filtered, the solution was freed from toluene and the residue was subjected to vacuum distillation over a 10 cm Vigreux column. 390 g (68% of the theoretical yield) of ethyl 2-(o-methylbenzyl)-acetoacetate of boiling point 100°-105° C. at 0.01 mm Hg were obtained.

EXAMPLE 2

Ethyl 2-chloro-2-(o-methylbenzyl)-acetoacetate 325 g (2.4 moles) of sulfuryl chloride were added dropwise to 511.0 g (2.2 moles) of ethyl 2-(o-methylbenzyl)-acetoacetate in the course of 2 hours, while stirring. Thereafter, the mixture was heated at 50° to 55° C. for 4 hours. The crude product was purified by vacuum distillation without a column. 547 g (92% of the theoretical yield) of ethyl 2-chloro-2-(o-methylbenzyl)-acetoacetate of boiling point 120° C. at 0.01 mm Hg were obtained.

EXAMPLE 3 o-Methylcinnamic acid 292 g (1.08 moles) of ethyl 2-chloro-2-(o-methylbenzyl)-acetoacetate were added dropwise to 4.85 moles of 25% strength aqueous NaOH solution in the course of 1 hour. The refluxed mixture was then stirred for a further 6 hours. The reaction solution was reacted twice by shaking with toluene and then acidified with semi-concentrated hydrochloric acid, and the precipitate which had separated out was filtered off under suction. It was rinsed with water and toluene and dried in a drying oven. 157 g (90% of the theoretical yield) of o-methylcinnamic acid of melting point 176° to 177° C. were obtained.

EXAMPLE 4

Phenylethyl o-methylcinnamate

A solution of 324.0 g (2.00 moles) of o-methylcinnamic acid, 428.0 g (3.5 moles) of 2-phenylethanol, 10.0 g (0.058 moles) of p-toluenesulfonic acid and 1,200 ml of toluene was refluxed under a water separator. After 15 hours, the calculated amount of water had separated off. The reaction solution was washed first with water and then with saturated sodium bicarbonate solution. The combined washwater was extracted once with ether, and the ether phase was combined with the organic phase. The combined, organic phases were fractionated over a 10 cm Vigreux column. The solvents were separated off under atmospheric pressure and in a vacuum from a water pump. The Vigreux column was replaced by a column head and the product was distilled under 0.01 mm Hg (b.p. 154°–155° C./0.01 mm Hg). 394.0 g of phenylethyl o-methylcinnamate of melting point 52° to 53° C. were obtained.

EXAMPLE 5

Floral perfume base having a gardenia character

| Parts by weight | |
|---|---|
| 20 | Crystalline -methylnaphthyl ketone |
| 15 | Diphenyl oxide |
| 20 | Cinnamyl alcohol |
| 80 | Isoamyl salicylate |
| 10 | Styryl acetate |
| 10 | Acetophenone, 10% strength in DPG |
| 20 | Anisaldehyde |
| 50 | Dimethylbenzylcarbinol |
| 15 | Dimethylbenzylcarbinyl acetate |
| 10 | Methylacetophenone, 10% strength in DPG |
| 50 | Phenylethyl alcohol |
| 60 | Pure ionone |
| 15 | Aldehyde C 11 (= undecanal), 20% strength in DPG |
| 20 | Aldehyde C 11 en (= 10-undecen-1-al), 20% strength in DPG |
| 15 | Aldehyde C 12 MNA (= 2-methylundecanal), 20% strength in DPG |
| 80 | Benzyl acetate |
| 110 | Alpha-amylcinnamaldehyde |
| 5 | Isoeugenol |
| 10 | Eugenol |
| 30 | Cananga oil |
| 100 | Synthetic rose |
| 55 | 8-Cyclohexadecenone |
| 100 | 2,2-Dimethyl-3-(m-methylphenyl)-propanol |
| 100 | Phenylethyl o-methylcinnamate |
| Total: 1,000 | |

EXAMPLE 6

Floral perfume base having a lilac character

| Parts of weight | |
|---|---|
| 280 | Terpineol |
| 160 | 2,2-Dimethyl-3-(m-methylphenyl)-propanol |
| 80 | Phenylethyl alcohol |
| 60 | Benzyl acetate |
| 5 | Anisaldehyde |
| 5 | Phenylacetaldehyde dimethyl acetal |
| 5 | Isoeugenol |
| 10 | Cinnamyl alcohol |
| 20 | Linatool |
| 80 | Hellotropin |
| 20 | Indole, 10% strength in dipropyleneglycol (DPG) |
| 70 | Benzyl alcohol |
| 40 | Ylang-Ylang oil synthetic |
| 20 | Cyclamen aldehyde |
| 5 | Aldehyde C 12 MNA (= 2-methylundecanal), 5% strength in DPG |
| 40 | 8-Cyclohexadecenone |
| 100 | Phenylethyl o-methylcinnamate |
| Total: 1,000 | |

While only several examples of the present invention have been described, it will be obvious to those skilled in the art that many modifications may be made to the present invention without departing from the spirit and scope thereof.

What is claimed is:

1. Phenylethyl o-methylcinnamate.
2. A fragrance composition, comprising phenylethyl o-methylcinnamate.
3. The fragrance composition according to claim 2, additionally including a carrier.

* * * * *